US008567403B1

(12) United States Patent
Lu et al.

(10) Patent No.: US 8,567,403 B1

(45) Date of Patent: Oct. 29, 2013

(54) BIOCHEMICAL AGENT FILTER USING ULTRAVIOLET IRRADIATION ON NANOPARTICLE-EMBEDDED IONIC GRIDS

(75) Inventors: Ryan P. Lu, San Diego, CA (US); Christopher K. Huynh, Rosemead, CA (US); Ayax D. Ramirez, Chula Vista, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 341 days.

(21) Appl. No.: 13/101,747

(22) Filed: May 5, 2011

(51) Int. Cl.
*A61M 11/00* (2006.01)

(52) U.S. Cl.
USPC ............ 128/205.27; 128/201.25; 128/201.28; 128/201.29; 250/493.1

(58) Field of Classification Search
USPC ......... 250/493.1–504 H; 128/205.27, 201.25, 128/206.17, 201.28, 201.29
See application file for complete search history.

(56) References Cited

U.S. PATENT DOCUMENTS

| | | | | |
|---|---|---|---|---|
| 4,378,499 | A * | 3/1983 | Spangler et al. | 250/287 |
| 6,233,748 | B1 * | 5/2001 | Gieger et al. | 2/410 |
| 8,397,715 | B2 * | 3/2013 | Litz | 128/201.25 |
| 8,513,630 | B2 * | 8/2013 | Ueno et al. | 250/504 R |
| 2010/0132715 | A1 * | 6/2010 | Litz | 128/207.12 |
| 2010/0213395 | A1 * | 8/2010 | Ueno et al. | 250/504 R |
| 2012/0279503 | A1 * | 11/2012 | Zhou et al. | 128/205.27 |

* cited by examiner

*Primary Examiner* — Steven Douglas

(74) *Attorney, Agent, or Firm* — Ryan J. Friedl; Kyle Eppele

(57) ABSTRACT

A system includes an ultraviolet light source, such as light-emitting diodes, disposed between a first ionic grid and a second ionic grid. The first and the second ionic grids have opposite ionic charges and a plurality of silver nanoparticles disposed thereon. The ultraviolet light source is configured to emit, onto the first and the second ionic grids, ultraviolet radiation having a wavelength of between about 100 nm and about 280 nm. A biochemical detector may be located adjacent to the first ionic grid on a side of the first ionic grid opposite the ultraviolet light source. The ultraviolet light source, first ionic grid, and second ionic grid may be located within a housing connected to a gas mask, and a membrane filter may be disposed between the gas mask and housing. The housing may include a power source connected to the ultraviolet light source.

15 Claims, 3 Drawing Sheets

BIOCHEMICAL AGENT FILTER USING ULTRAVIOLET IRRADIATION ON NANOPARTICLE-EMBEDDED IONIC GRIDS

FEDERALLY-SPONSORED RESEARCH AND DEVELOPMENT

The Biochemical Agent Filter Using Ultraviolet Irradiation on Nanoparticle-Embedded Ionic Grids is assigned to the United States Government and is available for licensing for commercial purposes. Licensing and technical inquiries may be directed to the Office of Research and Technical Applications, Space and Naval Warfare Systems Center, Pacific, Code 72120, San Diego, Calif., 92152; voice (619) 553-5118; email ssc_pac_T2@navy.mil; reference Navy Case Number 100760.

BACKGROUND

The absorbent capacity of a biochemical agent filter is typically the determining factor of a gas mask lifespan. These filters are generally based on activated carbon or other porous materials such as zeolites. Reliance upon passive methods of microbial eradication, such as filters with pore sizes smaller than the microbes, is not desirable. When the filter is saturated with hazardous chemicals it ceases to provide protection and the user may suffer a life-threatening injury. It is preferable to actively neutralize biological agents before they enter the gas mask filter. Currently however, there is no compact method to actively neutralize biological agents for gas masks. Accordingly, a need exists for an improved biochemical agent filter that may readily be integrated into a convention gas mask and that actively neutralizes biochemical agents before entering into the gas mask filter.

DETAILED DESCRIPTION OF SOME EMBODIMENTS

One or more of the embodiments disclosed herein involve a compact system that can attach to existing and future gas masks to filter out biochemical agents. The embodiments use ionizing grids embedded with silver nanoparticles to trap the biological threat and utilize radiation from ultra-violet (UV) light sources, such as light-emitting diodes (LEDs), to sanitize the ionizing grids. The biochemical agents are ionized and trapped on the grids and are neutralized by the silver nanoparticles. Microbials that are resistant to the silver nanoparticles are neutralized by the UV radiation, particularly UV-C radiation. The embodiments may be integrated into a compact battery powered unit.

Figure 1A:
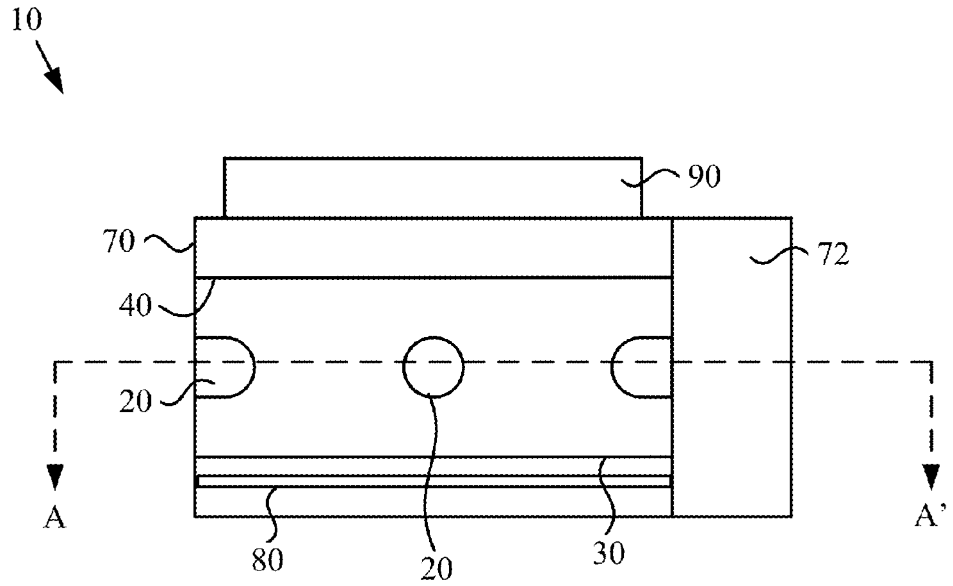
FIG. 1A shows a side view of an embodiment of a system in accordance with the Biochemical Agent Filter Using Ultraviolet Irradiation on Nanoparticle-Embedded Ionic Grids.
Figure 1B:
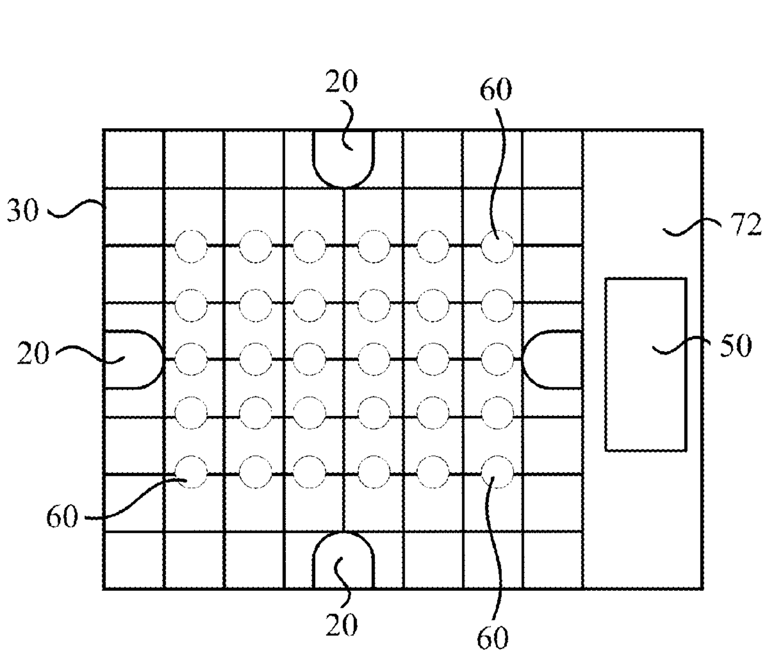
FIG. 1B shows a top view of a cross-section along line A-A' of the embodiment of the system shown in FIG. 1A, in accordance with the Biochemical Agent Filter Using Ultraviolet Irradiation on Nanoparticle-Embedded Ionic Grids.

Referring to FIGS. 1A and 1B, FIG. 1A shows a side view of an embodiment of a system 10 in accordance with the Biochemical Agent Filter Using Ultraviolet Irradiation on Nanoparticle-Embedded Ionic Grids. FIG. 1B shows a top view of a cross-section along line A-A' of system 10. System 10 includes a UV light source 20 disposed between a first ionic grid 30 and a second ionic grid 40. In some embodiments, UV light source 20 may comprise one or more light sources, as shown, such as LEDs. As an example, the LEDs may be selected from the group of LEDs consisting of III-nitride LEDs. The LEDs may also comprise Aluminum Gallium Nitride ($Al_xGa_{1-x}N$), where x is the percentage of Aluminum in the ternary compound and may be varied to adjust the energy bandgap to determine the wavelength of light emitted. UV light source 20 is configured to emit, onto first ionic grid 30 and second ionic grid 40, UV-C radiation, which is radiation having a wavelength of between about 100 nm and about 280 nm.

As shown in FIGS. 1A and 1B, system 10 may utilize four UV LEDs to achieve a balance of maximum germicidal effectiveness and efficient use of energy. However, any number of UV-C LEDs may be used between, on, or around the periphery of first ionic grid 30 and second ionic grid 40, depending upon system design and power output/efficiency specifications. A power source 50, such as a rechargeable battery, alkaline battery, or fuel cell, may be wired to UV light source 20. As an example, in embodiments where UV light source 20 comprises multiple LEDs, power source 50 may be wired individually to each LED.

First ionic grid 30 and second ionic grid 40 may be comprised of any conductive material, such as aluminum or stainless steel. Also, the shape of the spaces on each of grids 30 and 40 is not limited. As an example, grids 30 and 40 may contain square-shaped grid spaces. Further, the grid spacing on both grids 30 and 40 may be any size. As an example, grid spacing may be 1 mm. Additionally, the distance between first ionic grid 30 and second ionic grid 40 may be any desired length. As an example, the distance between grids may be 5 mm. It should be noted that, in some embodiments, system 10 is not limited to two ionic grids. Increasing the number of ionic grids improves the ability to capture biochemical agents and prevent them from passing through the system. In such multi-grid embodiments, each sequential ionic grid is charged with the opposite charge of the previous ionic grid.

First ionic grid 30 and second ionic grid 40 are configured to be charged by power source 50 to have opposite ionic charges. For example, first ionic grid 30 may have a negative charge and second ionic grid 40 may have a positive charge, or vice versa. Such a configuration causes biochemical agents passing through first ionic grid 30 to be ionized with the positive or negative charge on first ionic grid 30. The ionized biochemical agents will then be attracted to second ionic grid 40, which possesses an ionic charge opposite from the ionic charge on first ionic grid 30, and will attach to the surface of second ionic grid 40.

First ionic grid 30 and second ionic grid 40 are covered with silver nanoparticles 60, which may be deposited thereon. Silver nanoparticles 60 have anti-microbial properties that will neutralize most of the microbes that attach to the surface of second ionic grid 40. UV light source 20, which may comprise multiple LEDs located between first ionic grid 30 and second ionic grid 40, near the edges of the grids, will illuminate the grids and the space between the two grids. Such illumination will neutralize the microbes in transit to second ionic grid 40, as well as those microbes that have attached to the surface of second ionic grid 40 but were not neutralized by nanoparticles 60.

As shown, UV light source 20, first ionic grid 30, and second ionic grid 40 are contained within a housing 70. Housing 70 includes a power source compartment 72 for containing power source 50. Housing 70 may be any shape, including triangular, square, pentagonal, hexagonal, round, etc. System 10 may further include a biochemical detector 80 located adjacent to the first ionic grid 30 on a side of first ionic grid 30 opposite UV light source 20. Biochemical detector 80 functions to initially detect biochemical agents, allowing for UV light source 20 and/or first and second ionic grids 30 and 40, respectively, to be switched on only when biochemical agents are detected. The use of biochemical detector 80 helps provide for efficient use of power source 50. In such embodiments, a controller (not shown) may be connected to power source 50, biochemical detector 80, UV light source 20, and first and second ionic grids 30 and 40 to control the system to achieve the aforementioned power management benefits.

Figure 2:
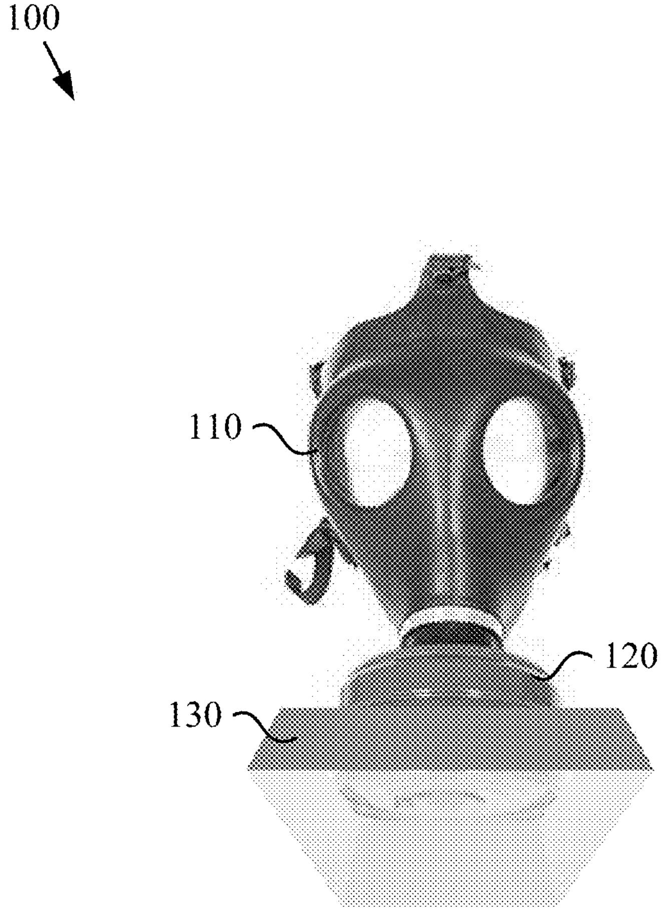
FIG. 2 shows a diagram of an embodiment of a system implemented on a gas mask, in accordance with the Biochemical Agent Filter Using Ultraviolet Irradiation on Nanoparticle-Embedded Ionic Grids.

System 10 may further include an airtight adapter 90 attached to the housing 70. Adapter 90 allows system 10 to interface with commercially available gas masks, such as that shown in FIG. 2. Referring to FIG. 2, FIG. 2 shows a diagram of an embodiment of a system implemented on a gas mask, in accordance with the Biochemical Agent Filter Using Ultraviolet Irradiation on Nanoparticle-Embedded Ionic Grids. System 100 includes a conventional gas mask 110 having a filter 120 attached thereto. A system 130, such as system 10 of FIGS. 1A and 1B, is connected to filter 120 via, for example, an airtight adapter, such as adapter 90 of system 10. In some embodiments, a membrane filter (not shown) is disposed between filter 120 and system 130. While FIG. 2 shows system 130 in front of filter 120, system 130 may also be placed between gas mask 110 and filter 120.

In other embodiments, system 130 may replace the standard gas mask filter 120 altogether with a thin membrane filter incorporated into system 130 that is configured to filter out micro-particles. The grids and membrane filter may also be replaceable by sliding them in and out. For hot swapping in the presence of biochemical agents, four grids should be the minimum, such that, one set may be active while the other set is inactive.

Figure 3:
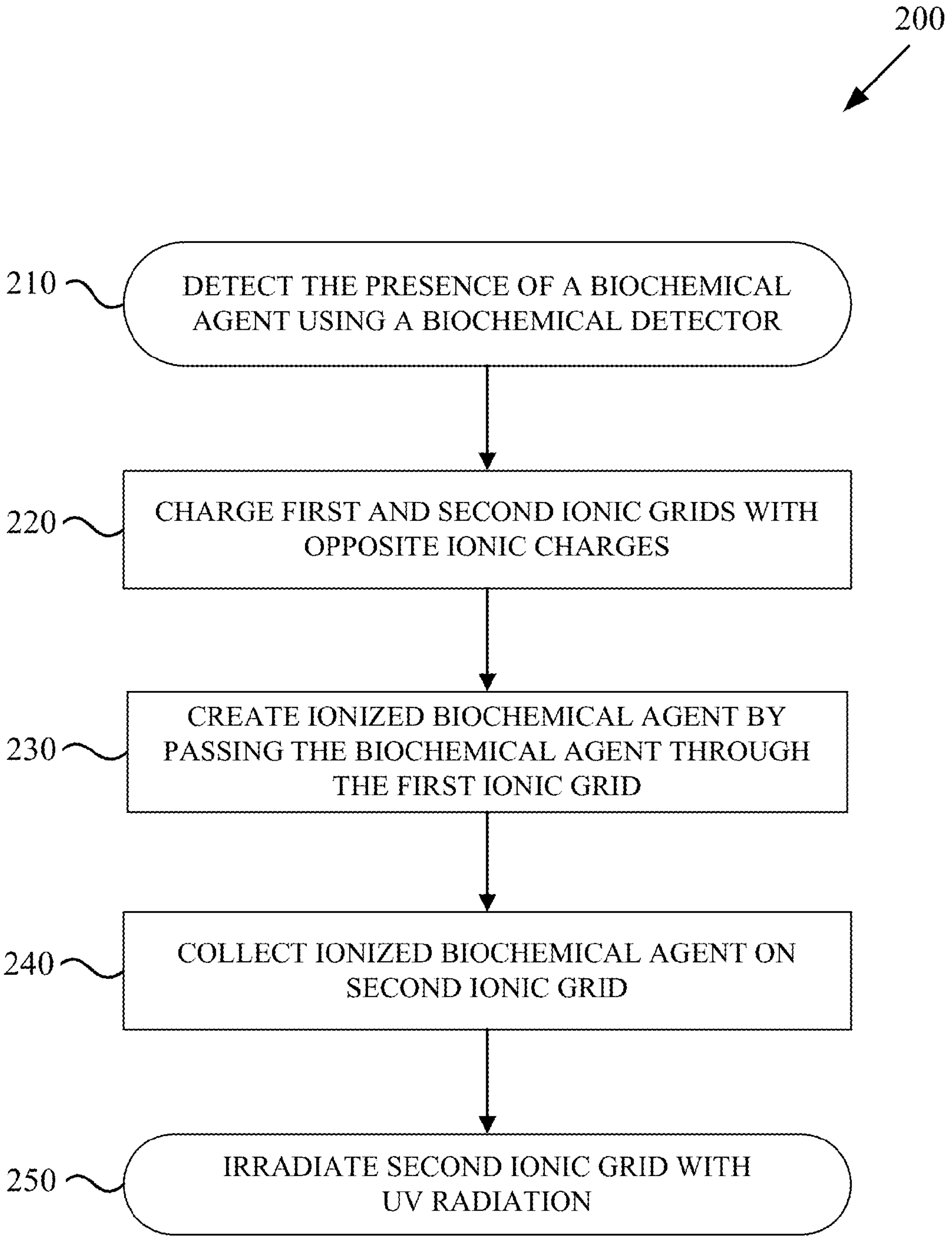
FIG. 3 shows a flowchart of an embodiment of a method in accordance with the Biochemical Agent Filter Using Ultraviolet Irradiation on Nanoparticle-Embedded Ionic Grids.

FIG. 3 shows a flowchart of an embodiment of a method 200 in accordance with the Biochemical Agent Filter Using Ultraviolet Irradiation on Nanoparticle-Embedded Ionic Grids. For illustrative purposes, method 200 will be discussed with reference to system 10. Method 200 may begin at step 210, which involves detecting the presence of a biochemical agent using biochemical detector 80. It should be recognized by one having ordinary skill in the art that the detection of particular biochemical agents, such as anthrax and mustard gas, will be dependent upon the particular biochemical sensor used, which is not limited in system 10. Next, step 220 involves using power source 74 to charge first ionic grid 30 and second ionic grid 40 with opposite ionic charges. For example, first ionic grid 30 is charged with a positive charge and second ionic grid 40 is charged with a negative charge. Method 200 may then proceed to step 230. It should be noted that in some embodiments, method 200 begins at step 230.

Step 230 involves creating an ionized biochemical agent by passing the biochemical agent through first ionic grid 30. The biochemical agent passes through first ionic grid 30 due to the grid spacing configuration of first ionic grid 30, which is not limited in the present disclosure. For example, the grid spacing may be 1 mm, as noted above, or may be smaller or larger as necessary. Upon passage through first ionic grid 30, the biochemical agent is ionized and is attracted to second ionic grid 40. Step 240 involves collecting the ionized biochemical agent on second ionic grid 40, which will occur due to the opposite charge of second ionic grid 40 in relation to first ionic grid 30. Method 200 may then continue to step 250, which involves irradiating, via UV light source 20, second ionic grid 40 with UV radiation having a wavelength of between about 100 nm and about 280 nm.

Although the system and method in accordance with the Biochemical Agent Filter Using Ultraviolet Irradiation on Nanoparticle-Embedded Ionic Grids have been discussed with reference to connection with conventional gas masks, the above-described systems and method may be used for other applications. For example, system 10 and method 200 may be incorporated into a stand-alone unit that may be used to purify air in various environments such as hospitals, office buildings, etc.

Many modifications and variations of the Biochemical Agent Filter Using Ultraviolet Irradiation on Nanoparticle-Embedded Ionic Grids are possible in light of the above description. Within the scope of the appended claims, the embodiments of the systems described herein may be practiced otherwise than as specifically described. The scope of the claims is not limited to the implementations and the embodiments disclosed herein, but extends to other implementations and embodiments as may be contemplated by those having ordinary skill in the art.

We claim:

1. A system comprising:

an ultraviolet light source disposed between a first ionic grid and a second ionic grid, the first and the second ionic grids having opposite ionic charges and a plurality of silver nanoparticles disposed thereon, the ultraviolet light source configured to emit, onto the first and the second ionic grids, ultraviolet radiation having a wavelength of between about 100 nm and about 280 nm.

2. The system of claim 1 further comprising a power source connected to the ultraviolet light source.

3. The system of claim 1, wherein the ultraviolet light source is one or more light-emitting diodes.

4. The system of claim 3, wherein the one or more light-emitting diodes are comprised of Aluminum Gallium Nitride ($Al_xGa_{1-x}N$), where x is the percentage of Aluminum in the ternary compound.

5. The system of claim 3, wherein the one or more light-emitting diodes are selected from the group of light-emitting diodes consisting of III-nitride light-emitting diodes.

6. The system of claim 1 further comprising a biochemical detector located adjacent to the first ionic grid on a side of the first ionic grid opposite the ultraviolet light source.

7. The system of claim 1 further comprising a housing connected to a gas mask, wherein the ultraviolet light source, the first ionic grid, and the second ionic grid are located within the housing.

8. The system of claim 7, wherein a membrane filter is disposed between the gas mask and the housing.

9. The system of claim 7, wherein the housing includes a power source compartment, the system further comprising a power source contained within the power source compartment and connected to the ultraviolet light source.

10. The system of claim 1, wherein the first ionic grid and the second ionic grid are spaced about 5 mm apart and each have a grid spacing of about 1 mm.

11. A system comprising:

a housing connected to a gas mask, the housing containing an ultraviolet light source disposed between a first ionic grid and a second ionic grid, the first and the second ionic grids having opposite ionic charges and a plurality of silver nanoparticles disposed thereon, the ultraviolet light source configured to emit, onto the first and the second ionic grids, ultraviolet radiation having a wavelength of between about 100 nm and about 280 nm, and a biochemical detector located adjacent to the first ionic grid on a side of the first ionic grid opposite the ultraviolet light source.

12. The system of claim 11, wherein the housing includes a power source compartment, the system further comprising a power source contained within the power source compartment and connected to the ultraviolet light source.

13. The system of claim 11, wherein the ultraviolet light source is one or more light-emitting diodes.

14. A method comprising the steps of:

creating an ionized biochemical agent by passing a biochemical agent through a first ionic grid having a first ionic charge and a plurality of silver nanoparticles disposed thereon;

collecting the ionized biochemical agent on a second ionic grid having an opposite ionic charge from the first ionic charge; and irradiating the second ionic grid with ultraviolet radiation having a wavelength of between about 100 nm and about 280 nm.

15. The method of claim 14 further comprising the steps of, prior to the step of creating an ionized biochemical agent:

detecting the presence of the biochemical agent using a biochemical detector; and upon detection of the biochemical agent, using a power source to charge the first and second ionic grids.

* * * * *